United States Patent
Su et al.

(10) Patent No.: US 6,897,195 B2
(45) Date of Patent: May 24, 2005

(54) COMPOSITION OF MENTHOL AND MENTHYL LACTATE, ITS PREPARATION METHOD AND ITS APPLICATIONS AS A COOLING AGENT

(75) Inventors: Evelyn G. Su, Nanjing (CN); Chang-Guo Wang, Nanjing (CN)

(73) Assignee: Nanjing Zhongshi Chemical Co., Nanjing (CN)

( * ) Notice: Subject to any disclaimer, the term of this patent is extended or adjusted under 35 U.S.C. 154(b) by 321 days.

(21) Appl. No.: 10/202,543

(22) Filed: Jul. 24, 2002

(65) Prior Publication Data

US 2004/0018954 A1 Jan. 29, 2004

(51) Int. Cl.[7] .............................................. A61K 7/46
(52) U.S. Cl. ........................... 512/1; 426/534; 426/650
(58) Field of Search ............................. 512/1; 426/534, 426/650

(56) References Cited

U.S. PATENT DOCUMENTS 6,509,007 B2 * 1/2003 Rajaiah et al. ................. 424/53
6,627,233 B1 * 9/2003 Wolf et al. ..................... 426/3

* cited by examiner

*Primary Examiner*—Monique T. Cole
(74) *Attorney, Agent, or Firm*—Clifford G. Frayne

(57) ABSTRACT

Disclosed here is a composition containing menthol and menthyl lactate, and its preparation method and its applications as a cooling agent and a flavoring agent.

The present invention provides a composition characterized in that it comprises menthol and menthyl lactate in a ratio by weight in the range of 1:4~4:1 and the corresponding crystallization point is below room temperature of 25° C. Such composition has the advantages of being liquid at room temperature; easy to use as a cooling agent or a flavoring agent; no need to use heat to melt menthol and menthyl lactate, which not only saves time, money and heating equipment, but also simplifies manufacturing process and can be used in cold processes at room temperature. The composition can be used as a cooling and/or flavoring agent and/or a fragrance ingredient in toothpaste, mouthwash, fragrance, cleansers, shaving cream, after shave products; shampoo, deodorant, antiperspirant, bath products, drinks, confectionary products, tobacco, pharmaceutical, foods, flavoring and fragrance products.

10 Claims, 1 Drawing Sheet

COMPOSITION OF MENTHOL AND MENTHYL LACTATE, ITS PREPARATION METHOD AND ITS APPLICATIONS AS A COOLING AGENT

BACKGROUND OF THE INVENTION

1. Field of the Invention

The present invention relates to the applications of menthol and its esters as cooling or flavoring or fragrance substances. In particular, this invention relates to a composition containing menthol and menthyl lactate having a crystallization point below room temperature and exhibits in liquid form at room temperature.

2. Description of the Prior Art

Menthol is a physiological cooling agent well known to the person skilled in the art for its analgesic, freshening and flavoring effects on the skin and/or the mucous membranes of the mouth.

Being a major constituent of peppermint oil, menthol has been used extensively in foods, beverages, dentifrices, mouthwashes, toiletries, lotions, confectionary, tobacco and pharmaceutical products. The disadvantages of using menthol, however, are its strong minty odor and the characteristic harsh notes it imparts to compositions in which it is found.

A need, therefore, exists for a cooling composition that will contribute a long-lasting cooling sensation to products without the unwanted harshness and unpleasant odor that come from menthol.

In order to overcome these disadvantages, various menthyl esters have been prepared. Unfortunately, most of these esters have disagreeable odors, making them unsuitable for use in a topical product. One exception is menthyl lactate, a known compound available from Haarman & Reimer GmBH (Germany) under the trade name of FRESCOLAT ML. According to the manufacturer, menthyl lactate only possesses a very faint inherent odor that does not affect the fragrancing of final products. The manufacturer's product literature indicates that Frescolat ML is a very effective active ingredient for use in cosmetic and food products. It was further pointed out that Frescolat ML is oil soluble and stable in the pH range of 4–8, and Frescolat ML should be added to emulsions at a temperature of around 40–45° C. To do this, it is necessary to melt Frescolat ML at a temperature of around 50–60° C. An additional option would be to first dissolve it in perfume oils, cosmetic oils or glycol solvents such as 1,2-propylene glycol or dipropylene glycol When adding Frescolat ML to shampoos, shower gels or foam baths, it is advisable to first dissolve it in perfume oil or glycol solvents. The resulting solution can then be mixed with the active washing substances. The general formula for Menthyl Lactate is shown as follows:

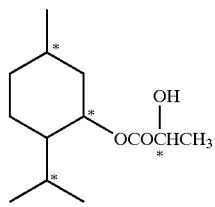

Compared to menthol, menthyl lactate has the advantages of low irritation, long-lasting cooling effect as well as low volatility. Nevertheless, menthyl lactate does not produce as strong a initial cooling effect as menthol, and therefore, its use has been limited to some extent, especially for oral care and skin care products, where the user desires to experience strong initial cooling effect as soon as the product is applied.

There have been reports in the technical literature where menthol and menthyl lactate have been used in the same formulation by adding menthol and menthyl lactate separately. For example, PCT WO 00/42983 describes a cosmetic composition containing menthol and menthyl lactate, having little odor and being non-irritating. The said composition comprises 0.01% to 2% by weight menthol and 0.1% to 10% by weight menthyl lactate, the menthol/menthyl lactate ratio lying in the range of 1/1 to 1/10, and being such that the odor of the menthol is barely perceivable, said composition not being irritating, in particular for the sensitive parts of the human body, while conserving the various beneficial effects of menthol. JP 06329528 and JP10231238 relates to cosmetic composition where menthol and menthyl lactate were used in the same formulation by adding them separately in a ratio of 1/1 and 2/1, respectively. In JP 06329528, the menthol and menthyl lactate concentration ranged from 0.1%:0.1% (1:1) to 0.2%:0.2% (1:1) in the examples, while it was claimed that menthol concentration can be in the range of 0.001–10.0% (w/w) and menthyl lactate can also be added in the range of 0.001–10.0%. In JP 10231238, it was reported that 0.2% menthol and 0.1% menthyl lactate be used in the same formulation with a ratio of 2:1.

The above-mentioned documents all describe the use of menthol and menthyl lactate by adding them separately into the formulation, and the concentration range is below 15%, and there is no mention about eutectic mixture formation in this formulation The disadvantage of such addition is that: menthol and menthyl lactate have to be melted first at a temperature of 50–60° C. or dissolved in perfume oils, cosmetic oils, or glycol solvents such as 1,2-propylene glycol or dipropylene glycol. The manufacturer's product information also mentioned that when adding Menthyl lactate to shampoos, shower gels or foam baths, it is advisable to first dissolve it in perfume oil or glycol solvents. The resulting solution can then be mixed with the active washing substances. Menthyl Lactate has been available from Haarman & Reimer GmBH (Germany) in two forms, crystalline form and non-crystalline form. The non-crystalline form has a congealing point of min. 40° C. and an appearance of solid, white substance with no additive, while the crystalline form has a congealing point of min. 42° C. and an appearance of white, crystalline powder with an additive of ~0.1% sodium bicarbonate. The non-crystalline form has the disadvantage of inconvenient handling because the product has to be melt in order to remove it from the container, which means that the container has to be heated together with the product. The crystalline form has the advantage of easy handling, but also has the disadvantages of an extra additive, which may cause compatibility problems in formulations and may need to be removed.

As can be seen from the above, menthol and menthyl lactate, if added separately in their respective normal solid form to the formulation, are not convenient to use. This is not favorable for large scale industrial manufacturing process. On one hand, such heating process needs to have dedicated equipment and heating facility to melt menthol and menthyl lactate, on the other hand, menthol and menthyl lactate, if added separately in their solid form, are not suitable for use in Cold Processing technologies, which is a growing trend in manufacturing in order to save energy and improve productivity. Furthermore, when heated up, menthol evaporates and generates strong minty odor that is disagreeable, and causes unfavorable health issues to workers handling it besides the losses of menthol.

OBJECTS OF THE INVENTION

An object of the present invention is to provide a composition containing menthol and menthyl lactate that are liquid at room temperature without any solvent or solubilizer, can be added directly into formulation in a liquid form without heating, non-irritating, of little odor and low volatility. Another object of the present invention is to provide a composition that delivers both excellent initial cooling sensation and long-lasting cooling effects in a formulation where it is used.

SUMMARY OF THE INVENTION

The above objects of the present invention can be achieved by mixing menthol and menthyl lactate in a certain ratio so that menthol and menthyl lactate forms a mixture with a crystallization point of the composition below room temperature and thus exhibits in liquid form at room temperature, whereas the menthol portion of the composition provides strong initial cooling sensation and the menthyl lactate portion provides the long-lasting cooling effects.

DETAILED DESCRIPTION OF THE INVENTION

Figure 1:
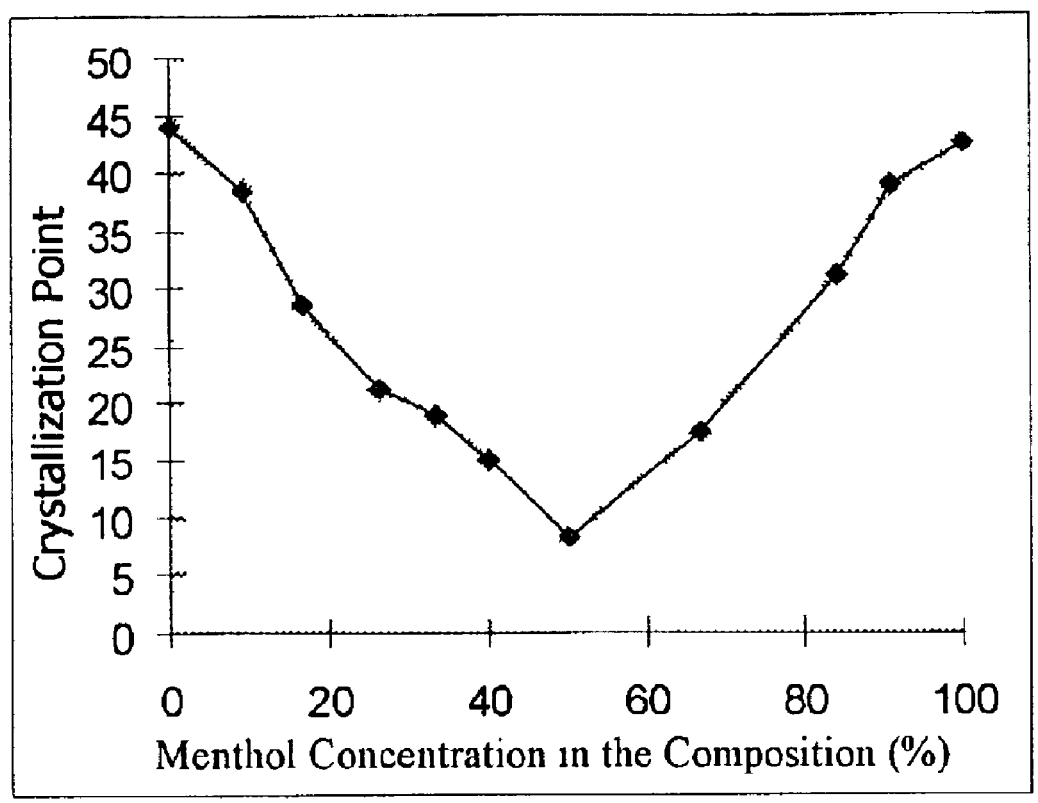
FIG. 1 illustrates the relationship of the crystallization point of the composition in the present invention as a function of menthol concentration.

Menthol can be obtained naturally from peppermint oil, or can be synthetic. Menthol contains three asymmetrical carbon atoms. It therefore exists in 12 different stereoisomers. However, only the L-menthol has been widely used, and its melting point is 39–43° C. Methyl lactate is obtained by reacting menthol with lactic acid to form the corresponding ester—menthyl lactate. Menthyl lactate contains 4 asymmetrical carbon atoms. It therefore exists in 16 different stereoisomers, whereas the commonly used ones are made from L-menthol and L-lactic acid or D-lactic acid. The commercially available product in the market is found to be L-menthyl L-lactate, with a melting point of 40–45° C.

In the context of this invention, the term "menthol" and "menthyl lactate" thus covers not only all such stereoisomers, but also any racemate or mixture of said stereoisomers. The following embodiments will use L-menthol and L-menthyl L-lactate as an example.

The inventors have been aware that menthol is known to form eutectic mixtures with a number of compounds, which result in a lower melting point of the eutectic mixture than any individual component. The eutectic mixture usually has a melting point around room temperature or higher. However, it has never been reported before that menthol and menthyl lactate form eutectic mixture. The current invention discloses for the first time an eutectic composition comprising menthol and menthyl lactate which is a liquid with a much lower crystallization point than the room temperature, and thus very useful for many applications. In order to achieve a crystallization point below room temperature, the ratio of the two substances has to be carefully controlled.

The present invention provides a composition containing menthol and menthyl lactate, with a ratio of menthol to menthyl lactate by weight lying in the range of 1:4~4:1 and a crystallization point lower than the room temperature of 25° C., preferably with a ratio of menthol to menthyl lactate by weight lying in the range of 3.5:6 5~6.5:3 5 and a crystallization point below 15 C; most preferably with a ratio of menthol to menthyl lactate by weight about 1:1 and the crystallization point not higher than 8.5° C.

According to the present invention, the mixture of menthol and menthyl lactate is in a liquid form at room temperature, and therefore, can be added to formulations directly without heating and saves time, energy and money and can be used conveniently in cold process manufacturing.

The present invention is achieved by the following procedure: menthol and menthyl lactate are weighed separately according to a certain ratio, and placed into the same container, stir at room temperature without heating until the resulting mixture becomes a clear, transparent liquid.

According to the present invention, the composition of menthol and menthyl lactate has the following advantages: the composition exhibits in liquid form at room temperature, and thus it is very convenient to use as a cooling agent in cosmetics, food and all other products. There is no need to heat and thus saves time, energy and money as well as simplifies the manufacturing process. In addition, it can be used in cold processing at ambient temperature, and thus resulting in significant savings in manufacturing time and costs.

The present invention provides a composition containing menthol and menthyl lactate as a cooling and/or flavoring agent, can also comprise the composition and other ingredients. The present invention can also be in the form of water dispersions or other forms of menthol and menthyl lactate, including, but not limited to, alcohol systems, cosmetic oils, silicone oils, esters or refined oils, etc; the present invention also provides a solution to systems or products where high concentrations of menthol and menthyl lactate are required but conventional method of incorporating these ingredients into the formulas can not provide sufficient solubility of menthol and menthyl lactate in the formulations. In particular, these systems with high concentrations of menthol and menthyl lactate may be used in toothpaste, mouthwash, fragrance, detergents, shaving cream, aftershave, shampoos, deodorants, antiperspirant, drinks, confectionary products (chewing gums), tobacco products as well as pharmaceutical preparations.

The above-mentioned composition can be achieved through the following procedure: Add the premixed composition containing menthol and menthyl lactate into suitable surfactants and mix, and then combine with water, oil or esters and homogenize.

The present invention can be utilized in many products with an impact on mucous membranes and skin, such as toothpastes, mouthwash, fragrances, detergents, shaving cream, after-shave, shampoos, bathing products, shower gels, deodorants, antiperspirant, drinks, chewing gum, tobacco and pharmaceutical preparations.

The present invention, as a cooling agent, has the advantages of providing both optimal initial cooling sensation as well as long lasting cooling effect.

The present invention will in the following be described more in detail with reference to a number of examples:

EXAMPLE 1

| Menthol | 50 g |
|---|---|
| Menthyl Lactate | 50 g |
| Total: | 100 g |

At room temperature of 23° C., 50 g of menthol and 50 g menthyl lactate in solid form were weighed into a beaker, and stirred slowly for 20 minutes, without heating, until the mixture became a clear, transparent liquid. The crystallization point of this mixture was measured and was found to be 8.2° C.

EXAMPLE 2

| Menthol | 25 g |
|---|---|
| Menthyl Lactate | 75 g |
| Total | 100 g |

At room temperature of 23° C., 25 g of menthol and 75 g menthyl lactate in solid form were weighed into a beaker, and stirred slowly for 20 minutes, without heating, until the mixture became a clear, transparent liquid. The crystallization point of this mixture was measured and was found to be 20.5° C.

EXAMPLE 3

| Menthol | 75 g |
|---|---|
| Menthyl Lactate | 25 g |
| Total: | 100 g |

At room temperature of 23° C., 75 g of menthol and 25 g menthyl lactate in solid form were weighed into a beaker, and stirred slowly for 20 minutes, without heating, until the mixture became a clear, transparent liquid. The crystallization point of this mixture was measured and was found to be 21.1° C.

EXAMPLE 4

| Mixture from Example 1 | 10 g |
|---|---|
| Tween 60 (Polysorbate 60) | 3 g |
| Water | 87 g |
| Total: | 100 g |

Into a container, add 10 g of the resulting mixture from Example 1, 3 g of Tween 60 and 87 g of water, homogenize at room temperature at a speed of 5000 rpm, to obtain a stable, milky white emulsion—a water dispersion containing 10% menthol and menthyl lactate.

EXAMPLE 5

| Mixture from Example 1 | | 10 g |
|---|---|---|
| Phospholipid SV (Stearamidopropyl PG-Dimonium Chloride Phosphate (and) Cetyl Alcohol) | 3.6 g | |
| Brij 72 (Steareth-2) | 3.6 g | |
| Water | Balance to | 100 g |

Into a container, add 10 g of the resulting mixture from Example 1, 3.6 g of Phospholipid SV and 3.6 g Brij 72, and water to make 100 g, homogenize at room temperature under high pressure and high shear using a microfluidizer, to obtain a stable, milky white emulsion—a water nano-dispersion containing 10% menthol and menthyl lactate.

EXAMPLE 6

| Mixture from Example 1 | 20 g |
|---|---|
| Span 80 (Sorbitan Oleate) | 5 g |
| Dimethicone | 75 g |
| Total: | 100 g |

Into a container, add 20 g of the resulting mixture from Example 1, 5 g of Span 80 and 75 g of Dimethicone, homogenize at room temperature at a speed of about 5000 rpm, to obtain a stable, milky white emulsion—a silicone oil dispersion containing 20% menthol and menthyl lactate.

While the present invention has been described with respect to the exemplary embodiments thereof, it will be recognized by many of ordinary skill in the art that many modifications and changes can be made without departing from the spirit and scope of the invention. Therefore it is manifestly intended that the invention be limited only by the scope of the claims and the equivalence thereof.

We claim:

1. A composition of matter for use as a cooling agent, flavoring agent or fragrance agent, comprising a eutectic mixture of menthol and menthyl lactate in a weight ratio of said menthol to said menthyl lactate in the range of 1:4~4:1 with a concentration of 20% to 80% menthol and 80% to 20% menthyl lactate by weight, said mixture having a crystallization point below 25° C.

2. A composition of matter in accordance with claim 1 wherein said weight ration of menthol to menthyl lactate is preferably in the range from 3.5:6.5 to 6.5:3.5 with a concentration of 35% to 65% menthol and 65% to 35% menthyl lactate by weight, said mixture having a crystallization point below 15° C.

3. A composition of matter for use as a cooling agent or flavorinq agent in accordance with claim 2 wherein said preferred weight ration of said menthol to said menthyl lactate being 1:1 with a concentration of 50% menthol and 50% menthyl lactate by weight and having a crystallization point below 8.5° C.

4. A composition of matter for use as a cooling agent or flavoring agent in accordance with claim 1, said weight ration of said menthol and said menthyl lactate include stereoisomers thereof.

5. A composition of matter in accordance with claim 3 or 4 for use as a cooling agent in skin care products, wherein a eutectic mixture of menthol and menthyl lactate exists in the formulation to give rise to higher solubility of menthol and menthyl lactate than otherwise possible.

6. A composition of matter in accordance with claim 3 or 4 for use as a flavoring agent, wherein a eutectic mixture of menthol and menthyl lactate exists in the formulation to give rise to higher solubility of menthol and menthyl lactate than otherwise possible.

7. A composition of matter in accordance with claim 3 or 4 for use in fragrance products, wherein a eutectic mixture of menthol and menthyl lactate exists in the formulation to give rise to higher solubility of menthol and menthyl lactate than otherwise possible.

8. A method of manufacture of a composition of matter for use as a cooling agent, flavoring agent or fragrance agent comprising the following steps:
   a. Introducing menthol and menthyl lactate into a mixer in a weight ration range of 1:4~4:1;
   b. Stir at low rpm at room temperature to form a uniform eutectic mixture;
   c. Remove contents from mixer after achieving a clear transparent liquid;
   d. Mix contents of step c with suitable carrier for formulating said cooling agent, flavoring agent or fragrance agent; e. Repeat steps a–c as required.

9. The method of manufacture in accordance with claim 8 wherein the weight ratio of menthol to menthyl lactate in step (a) is in the range of 3.5:6.5 to 6.5:3.5.

10. The method of manufacture in accordance with claim 8 wherein the weight ration of menthol to menthyl lactate in step (a) is 1:1.

* * * * *